United States Patent [19]

Joseph et al.

[11] Patent Number: 5,559,329

[45] Date of Patent: Sep. 24, 1996

[54] SCANNING ELECTRON MICROSCOPE FIBER PUSH-OUT APPARATUS AND METHOD

[75] Inventors: Brian E. Joseph; Russell P. Stackpole, II; Everett H. Baker, all of Wheeling, W. Va.

[73] Assignee: Touchstone Research Laboratory, Ltd., Triadelphia, W. Va.

[21] Appl. No.: 298,572

[22] Filed: Aug. 31, 1994

[51] Int. Cl.$^6$ .................................................... H01J 37/28
[52] U.S. Cl. .......................... 250/306; 250/307; 250/310; 73/842
[58] Field of Search .................................... 250/306, 307, 250/310, 311; 73/842

[56] References Cited

U.S. PATENT DOCUMENTS

| | | | |
|---|---|---|---|
| 4,632,864 | 12/1986 | Cordova et al. | 428/265 |
| 4,662,228 | 5/1987 | Tse | 73/842 |
| 4,848,141 | 7/1989 | Oliver et al. | 73/81 |
| 4,972,720 | 11/1990 | Wu | 73/801 |
| 5,361,641 | 11/1994 | Eldridge et al. | 73/842 |

OTHER PUBLICATIONS

*Continuous Ceramic Fiber Aluminum Matrix Composites*, pp. 1–6, 3M.

J. I. Eldridge et al., *Fiber Push–out Testing Apparatus for Elevated Temperatures*, pp. 1035–1042, Apr. 1994, J. Mater. Res., vol. 9, No. 4.

A. M. Daniel et al., *A Scanning Electron Microscope Based Microindentation System*, pp. 632–638, Mar. 1994, Rev. Sci. Instrum., vol. 85, No. 3.

*The Nano Indenter™ II*, pp. 1–6, Nano™ Instruments, Inc.

G. M. Pharr et al., *Measurement of Thin Film Mechanical Properties Using Nanoindentation*, pp. 28–33, Jul. 1992, Materials Research Society Bulletin, vol. 17, No. 7.

W. C. Oliver et al., *An Improved Technique for Determining Hardness and Elastic Modulus Using Load and Displacement Sensing Indentation Experiments*, pp. 1564–1583, Jun. 1992, J. Mater. Res., vol. 7, No. 6.

D. B. Marshall et al., *Measurement of Interfacial Debonding and Sliding Resistance in Fiber Reinforced Intermetallics*, pp. 443–454, 1992, Acta metall. mater., vol. 40, No. 3.

J. I. Eldridge, *Desktop Fiber Push–Out Apparatus*, pp. 1–11, Dec. 1991, NASA Technical Memorandum 105341.

(List continued on next page.)

*Primary Examiner*—Bruce C. Anderson
*Attorney, Agent, or Firm*—Kirk D. Houser; Eckert Seamans Cherin & Mellott

[57] ABSTRACT

The application discloses an apparatus for measuring interfacial properties of a fiber-matrix composite material, such as a ceramic-matrix, metal-matrix or continuous fiber metal-matrix composite; or a support material, such as a fiber-optic fiber support medium. The apparatus includes a linear motion feedthrough having an indentor for pushing a fiber end, a load cell for sensing debonding and frictional sliding loads, and a scanning electron microscope (SEM) for magnifying the material in order to align the indentor with the fiber end. The feedthrough may push the fiber at a predetermined velocity with up to about a 20 pound load force. The SEM may include a vacuum chamber for housing the material, the indentor, the load cell, and a hot stage module. The hot stage module may increase the temperature of the material to about 1500° C. The apparatus may also include a data acquisition computer for recording the force with respect to time as the fiber is pushed out of the matrix, an acoustic sensor for recording a time when the fiber is debonded from the matrix, and an imaging computer for recording an image of the material. Alternatively, an apparatus may measure a bending or a crushing force which is applied to a fiber shaft by an indentor. Alternatively, a method may sense interfacial properties of a composite material including a plurality of fibers in a matrix having a diameter less than about 10 μm.

20 Claims, 7 Drawing Sheets

OTHER PUBLICATIONS

P. D. Jero et al., *Effect of Interfacial Roughness on the Frictional Stress Measured Using Pushout Tests*, pp. 1–9, Nov. 1991, Journal of the American Ceramic Society, vol. 74, No. 11.

T. P. Weihs et al., *Experimental Examination of the Push–Down Technique for Measuring the Sending Resistance of Silicon Carbide Fibers in a Ceramic Matrix*, pp. 524–534, Mar. 1991, Journal of the American Ceramic Society, vol. 74, No. 3.

J. D. Bright et al., *Interfacial Sliding Friction in Silicon Carbide–Borosilicate Glass Composites: A Comparison of Pullout and Pushout Tests*, pp. 115–122, Jan. 1991, Journal of the American Ceramic Society, vol. 74, No. 1.

G. Morscher et al., *Temperature Dependence of Interfacial Shear Strength in SiC–Fiber–Reinforced Reaction–Bonded Silicon Nitride*, pp. 713–718, Mar. 1990, Journal of the American Ceramic Society, vol. 73, No. 3.

D. C. Cranmer et al., *Comparison of Methods for Determining Fiber/Matrix Interface Frictional Stresses in Ceramic Matrix Composites*, pp. 124–135, 1990, ASTM STP 1080.

D. B. Marshall et al., *An Indentation Method for Measuring Residual Stresses in Fiber–reinforced Ceramics*, pp. 95–103, 1990, Materials Science and Engineering, A126.

J. D. Bright et al., *Interfacial Bonding and Friction in Silicon Carbide (Filament)–Reinforced Ceramic–and Glass–Matrix Composites*, pp. 1891–1898, Oct. 1989, Journal of the American Ceramic Society, vol. 72, No. 10.

D. B. Marshal et al., *Measurement of Interfacial Mechanical Properties in Fiber–Reinforced Ceramic Composites*, pp. 542–548, Aug. 1987, Journal of the American Ceramic Society, vol. 70, No. 8.

P. D. Warren et al., *Design, Analysis and Application of An Improved Push–through Test for the Measurement of Interface Properties in Composites*, pp. 1–30, Materials, University of California.

D. B. Marshal et al., *Interfacial Properties and Residual Stresses in Titanium and Titanium Aluminide Matrix Composites*, pp. 1–19, Rockwell International Science Center.

T. W. Clyne et al., *Interfacial Mechanical Testing of Metal Matrix Composites*, pp. 127–139, University of Cambridge.

M. H. Lewis et al., *Microstructure–property Relationships in Silicate–matrix Composites*, pp. 109–118, Journal of Microscopy, vol. 169, Pt. 2, Feb. 1993.

A. M. Daniel et al., *Measurement of Interfacial Micromechanics in Fibre Reinforced Ceramic Matrix Composites*, pp. 131–138, Ceram. Eng. Sci. Proc. 14, Jul.–Aug., 1993.

M. H. Lewis et al., *Microstructure and Macromechanical Behaviour of CMC's*, pp. 10-1–10-13, Introduction of Ceramics into Aerospace Structural Composites, Proceedings of the AGARD/NATO Workshop, Apr. 1993.

M. G. Cain et al., *Presynthesised Interfaces for Ceramic Matrix Composites via Fibre Coating*, pp. 246–252, Materials Letters, vol. 17, No. 5, Sep. 1993.

A. M. Daniel et al., *Measurement of Interfacial Micromechanics in Ceramic Matrix Composites*, pp. 108–113, British Ceramic Transactions, vol. 93, No. 3, Mar. 1994.

SCANNING ELECTRON MICROSCOPE FIBER PUSH-OUT APPARATUS AND METHOD

This invention relates to a device for measuring properties of a support material. More particularly, this invention relates to such a device for sensing interfacial properties of a fiber-matrix composite material whenever individual fibers are pushed with respect to the matrix. This invention also relates to a device for measuring properties of a fiber for the fiber-matrix composite material. This invention further relates to a method for sensing interfacial properties of the fiber-matrix composite material.

Advanced composite materials (e.g., metal-matrix composites, polymer-matrix composites, ceramic-matrix composites, etc.) include a plurality of high strength fibers in a surrounding metal, polymer or ceramic matrix. The mechanical properties of the fiber-matrix interface are a critical parameter which governs the overall behavior of the composite material. The bond strength, for example, between the fibers and the matrix determines whether the composite material is brittle (for a relatively high bond strength) or is relatively ductile (for a relatively low bond strength).

Characterizing the fiber-matrix interface yields several insights into the bulk mechanical properties of the composite (e.g., ultimate strength, fatigue life, creep behavior, crack growth, etc.). Generally, fiber debonding and sliding affect both the strength and the toughness of the composite. The bond strength (i.e., the fiber-matrix interfacial shear strength), which controls debonding of the fiber-matrix system, is one of the determining factors in composite strength. Interfacial frictional stress between the fiber and the matrix affects the fatigue life, the load carrying capability, and fiber movement in the matrix after the occurrence of debonding.

The interfacial shear strength and frictional stress may be utilized to determine the degree of the chemical bond between the fiber and the matrix (i.e., the chemical attack). These two parameters may also facilitate analysis of residual stress effects between the fiber and the matrix. These parameters, also, predict toughness due to fiber slippage in the matrix, crack growth resistance/blunting, and creep resistance of the composite material when a strong interface strength is present. Other uses include the characterization of composite material samples after tensile, fatigue or creep testing as a failure analysis tool.

Characterizing the fiber-matrix interface is helpful in understanding the performance of the interface in service (e.g., by interface testing at elevated temperatures, after fatigue loading, etc.). A variety of proposals have been advanced for characterizing the fiber-matrix interface (e.g., fiber push-out, fiber push-in (indentation), fiber pull-out, and techniques involving calculations based on bend testing).

A fiber pull-out test involves the tensile loading of a single fiber in order to pull the fiber from its surrounding matrix at room temperature. A fiber push-in test involves the use of a diamond indentor (e.g., a Vickers diamond) to push a single fiber a limited distance into the matrix at room temperature. A fiber push-out test normally involves the use of a flat-bottomed indentor or punch which pushes a single fiber through its surrounding matrix in order to displace the fiber a distance of at least one fiber diameter.

One instrument is known to attempt fiber push-out tests on 10–20 µm Nicalon (SIC) fibers and selected 12 µm oval Nextel fibers at room temperature using conventional microscopes for alignment of a 12 µm indentor with the end of the fiber. Another set of instruments is also known to conduct fiber push-out tests on 140 µm scs-6 (sic) fibers and 140–150 µm Saphikon ($Al_2O_3$) fibers at room temperature and up to about 900° C. using conventional microscopes for alignment of a 25–100 µm indentor with the end of the fiber. It is further known to attempt fiber push-out tests on 50–60 µm fibers at such temperatures using such conventional microscopes.

J. I. Eldridge, *Desktop Fiber Push-Out Apparatus*, NASA Technical Memorandum 105341, December 1991, discloses an apparatus for performing fiber push-out testing on continuous fiber-reinforced composites at room temperature. A stereo microscope having a television camera produces a magnification factor of 31.5 for alignment of a fiber and an indentor.

J. I. Eldridge et al., *Fiber Push-Out Testing Apparatus for Elevated Temperatures*, Journal of Materials Research, April 1994, discloses an apparatus for performing fiber push-out testing on continuous fiber-reinforced composites at room and elevated temperatures. The apparatus heats a composite specimen to up to 1100° C. in a vacuum of $10^{-6}$ Torr. An optical microscope is utilized to align a 142 µm fiber with a 100 µm indentor.

We provide an apparatus for use in measuring properties of a fiber-matrix composite material including a plurality of fibers in a matrix. We provide a pushing mechanism for pushing an end of an individual fiber of the plurality of fibers with respect to the matrix. We also provide a sensor for sensing at least one interfacial property of the fiber-matrix composite material whenever the individual fiber is pushed with respect to the matrix. We further provide an electron microscope for magnifying the fiber-matrix composite material in order to align the pushing mechanism with the end of the individual fiber.

We may provide an apparatus for use in measuring properties of individual fibers having a diameter less than about 10 µm. We may also provide a pushing mechanism which includes a linear motion feedthrough. We may further provide a linear motion feedthrough which includes an indentor for pushing the end of the individual fiber at a predetermined velocity and a drive controller for controlling the predetermined velocity. We may also provide a pushing mechanism which includes an indentor having a diameter of about 7 µm for pushing the end of the individual fiber.

We may provide an electron microscope which includes a vacuum chamber for housing the fiber-matrix composite material. We may also provide an indentor which is housed within the vacuum chamber for pushing the end of the individual fiber. We may further provide a sensor which includes a load cell that is housed within the vacuum chamber for sensing at least one of a debonding load between the individual fiber and the matrix and a frictional sliding load between the individual fiber and the matrix.

We may provide a pushing mechanism for pushing the individual fiber out of the matrix. We may also provide a sensor which includes a load cell housed within the vacuum chamber for sensing a force applied by the indentor to the end of the individual fiber. We may further provide a sensor including a data acquisition mechanism for recording the force with respect to time as the individual fiber is pushed out of the matrix. We may also provide a pushing mechanism which places up to about a 20 pound load force on the end of the individual fiber. We prefer to provide an indentor having a flat bottom diameter of about 7 µm for fibers having a diameter of about 10 µm.

We may provide an acoustic emission sensor housed within the vacuum chamber for recording a time when the individual fiber is debonded from the matrix. We may also provide a sensor including an imaging mechanism for recording an image of the individual fiber and at least part of the matrix at about the time when the individual fiber is debonded from the matrix.

We may provide an electron microscope including a hot stage module which is housed within the vacuum chamber for increasing the temperature of the fiber-matrix composite material. We may also provide a hot stage module which increases the temperature of the fiber-matrix composite material to about 1500° C.

Alternatively, we may provide an apparatus for use in measuring properties of a fiber-matrix composite material including a plurality of fibers in a matrix having a diameter less than about 10 µm. We may also provide a pushing mechanism for pushing an end of at least one fiber with respect to the matrix. We may further provide a sensor for sensing an interfacial property of the fiber-matrix composite material whenever the at least one fiber is pushed with respect to the matrix. We may also provide a magnification mechanism for magnifying the fiber-matrix composite material in order to align the pushing mechanism with the end of the at least one fiber.

Alternatively, we may provide an apparatus for use in measuring properties of a fiber for a fiber-matrix composite material including a shaft having a diameter less than about 10 µm. We may also provide a pushing mechanism for pushing the shaft of the fiber. We may further provide a sensor for sensing a force applied by the pushing mechanism to the shaft of the fiber. We may also provide a magnification mechanism for magnifying the shaft of the fiber in order to align the pushing mechanism with the shaft of the fiber.

We may provide a magnification mechanism including a first support for supporting a first support point of the shaft and a second support for supporting a second support point of the shaft. We may also provide a pushing mechanism for pushing a shaft push point, which is between the first support point and the second support point, in order to bend the fiber. We may further provide a sensor which senses a bending force which is applied to the shaft by the pushing mechanism.

We may provide a magnification mechanism which includes a support for supporting at least part of the shaft. We may also provide a pushing mechanism which pushes the shaft of the fiber in order to crush the shaft against the support. We may further provide a sensor which senses a crushing force which is applied to the shaft by the pushing mechanism.

Alternatively, we may provide a method for sensing at least one interfacial property of a fiber-matrix composite material including a plurality of fibers in a matrix having a diameter less than about 10 µm. We may also provide the steps of magnifying the fiber-matrix composite material in order to identify an end of an individual fiber of the plurality of fibers, aligning an indentor with the end of the individual fiber, pushing the end of the individual fiber with respect to the matrix with the indentor, and sensing at least one interfacial property of the fiber-matrix composite material whenever the individual fiber is pushed with respect to the matrix.

We may provide for pushing the individual fiber into the matrix at a predetermined velocity. We may also provide for sensing a force that is applied to the end of the individual fiber. We may further provide the step of recording the force with respect to time whenever the individual fiber is pushed into the matrix.

We may also provide the steps of recording an image of the individual fiber and at least part of the matrix, recording a time when the individual fiber is debonded from the matrix, and pushing the individual fiber out of the matrix with the indentor. We may further provide the step of increasing the temperature of the fiber-matrix composite material to a preselected temperature.

Alternatively, we may provide an apparatus for use in measuring properties of a support material including at least one member which is supported by the support material. The at least one member may have a surface. The surface may have a dimension which is less than about 10 µm. We may also provide a pushing mechanism for pushing the surface of the at least one member with respect to the support material. We may further provide a sensor for sensing at least one property of the at least one member whenever the at least one member is pushed with respect to the support material. We may also provide an electron microscope for magnifying the support material in order to align the pushing mechanism with the surface of the at least one member.

Other details, objects, and advantages of our invention will become more apparent as the following description of a present preferred embodiment thereof proceeds.

In the accompanying drawings, we have illustrated a present preferred embodiment of our invention in which.

Figure 1:
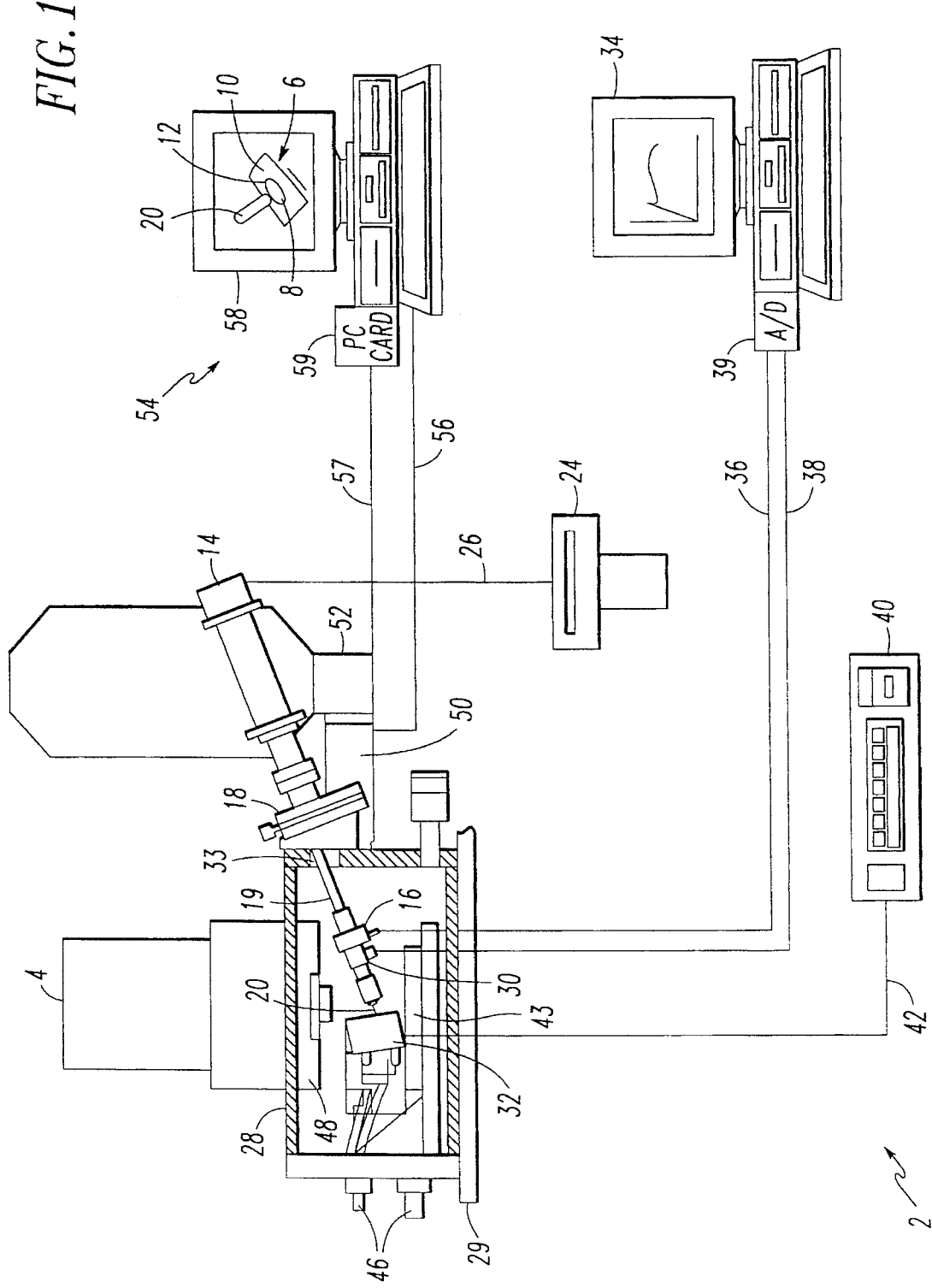
FIG. 1 is a schematic diagram of a fiber push-out apparatus including a scanning electron microscope in accordance with the invention.

A schematic diagram of a fiber push-out apparatus 2 including a scanning electron microscope (SEM) 4 is shown in FIG. 1. The apparatus 2 measures properties of a fiber-matrix composite material 6 as further shown in FIG. 2. A non-limiting example of the composite material 6 is disclosed in *Continuous Ceramic Fiber Aluminum Matrix Composites*, published by 3M, which is incorporated herein by reference. The composite material 6 includes a plurality of fibers 8 in a support material or matrix 10 which surrounds the fibers 8. Each of the fibers 8 has a generally circular end 12, it being understood that the invention is applicable to a wide variety of fiber-matrix composite materials (e.g., metal-matrix composites, polymer-matrix composites, ceramic-matrix composites, etc.) including individual fibers having oval ends or bundles of twisted fibers having a bundled end, and, also, to a wide variety of support materials (e.g., a fiber-optic cable, an integrated circuit, a micro-machine, etc.) including a member (e.g., a fiber-optic fiber, a bond lead, a micro-machine gear or axle, etc.) which is supported by the support material.

The apparatus 2 also includes a linear motion feedthrough 14 and a miniature load cell 16. The linear motion feedthrough 14 includes an alignment guide 18 and a feedthrough shaft 19. The exemplary linear motion feedthrough 14 is manufactured by Huntington Mechanical Laboratories as model MFL-275-4. The exemplary load cell 16 is manufactured by Sensotec as Model 31 and has a 25 pound load force capacity. Alternatively, a 5 pound load force capacity load cell may be provided. The alignment guide 18 aligns the feedthrough shaft 19 within the SEM 4. The load cell 16 is connected on the linear axis of the feedthrough shaft 19.

Figure 2:
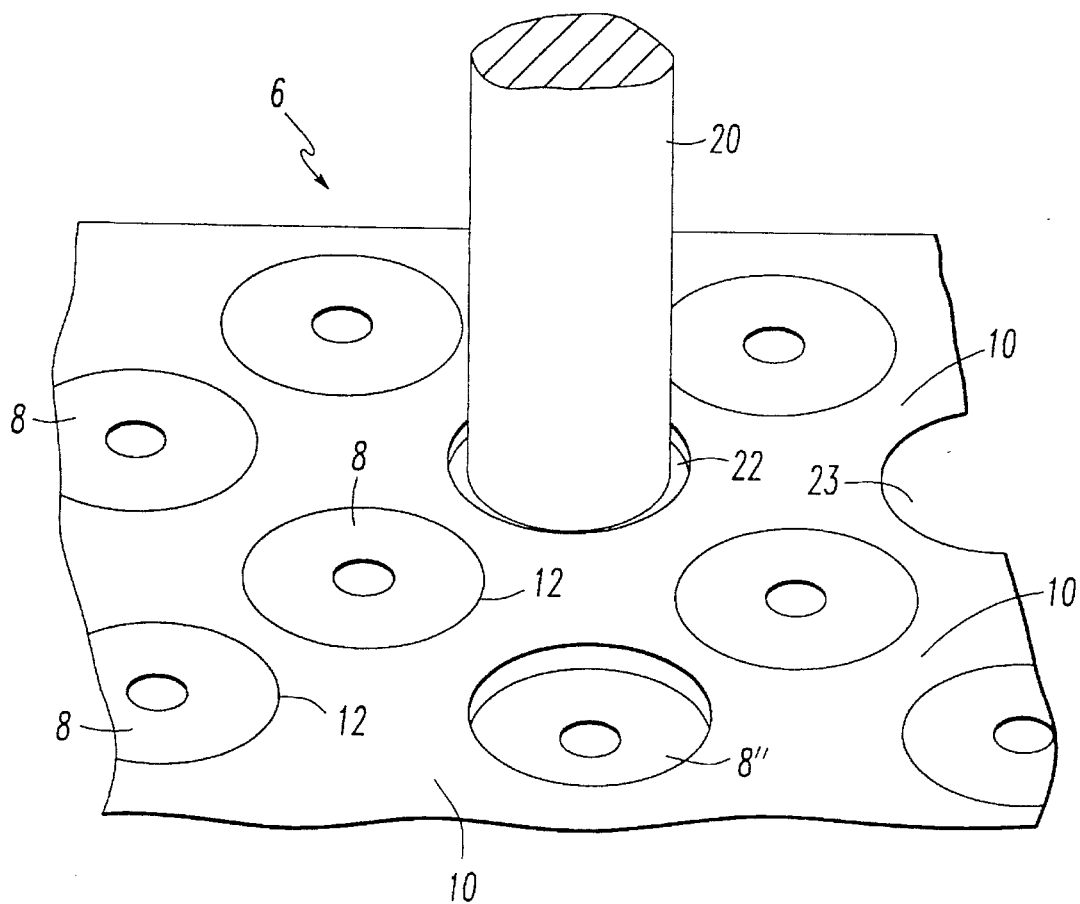
FIG. 2 is an isometric view of an indentor for pushing a fiber with respect to a fiber-matrix composite material.
Figure 4:
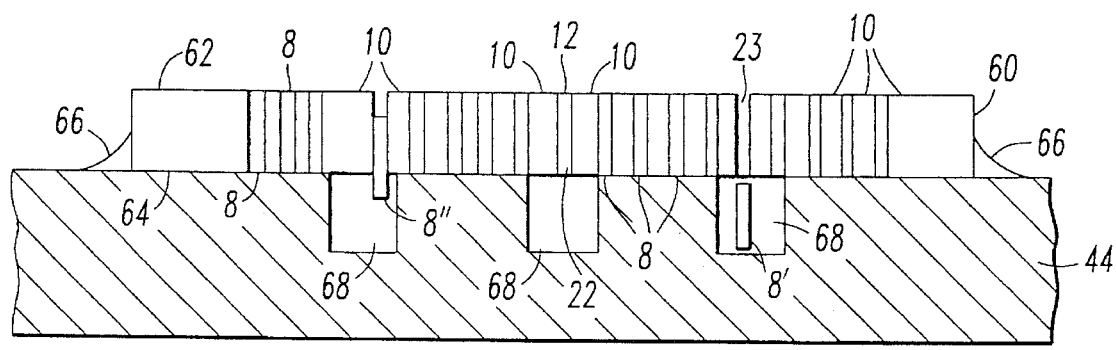
FIG. 4 is a partial cross-sectional view along line IV—IV of FIG. 3.

As best shown in FIG. 2, the linear motion feedthrough 14 also includes an indentor 20 for pushing the end 12 of an individual fiber 22 of the fibers 8 with respect to the matrix 10, it being understood that the invention is applicable to both push-in and push-out tests. As shown in FIG. 4, the matrix 10 includes a location 23 which was previously occupied by a fiber 8' that was pushed from the matrix 10. As further shown in FIG. 4, the matrix 10 also includes a fiber 8" which was pushed into the matrix 10.

The exemplary indentor 20, which is suitable for fibers having a diameter smaller than 20 μm, is a conical diamond indentor manufactured by Gilmore Diamond. The exemplary indentor 20 has a flat bottom diameter of 7 μm and a cone angle of 70 degrees Alternatively, for fiber diameters 20 μm and larger, a micrograin tungsten carbide punch manufactured by National Jet Company may be used in place of the exemplary indentor 20. The indentor 20 may, furthermore, have a range of sizes which are suited for the diameter of the fiber 22. Preferably, the diameter of the indentor 20 is selected to be approximately 70% of the fiber diameter (e.g., a 7 μm indentor diameter for a 10 μm fiber diameter) in order to allow a uniform load distribution on the generally circular end 12 of the exemplary fiber 22.

Continuing to refer to FIGS. 1–2, the load cell 16 senses interfacial properties of the fiber-matrix composite material 6 whenever the individual fiber 22 is pushed with respect to the matrix 10. The SEM 4 magnifies the fiber-matrix composite material 6 in order to align the inventor 20 with the end 12 of the individual fiber 22. Accordingly, the SEM 4 of the apparatus 2 permits easy alignment of the indentor 20 with the end 12 of the fiber 22 for testing of the composite material 6.

The linear motion feedthrough 14 also includes a drive controller 24 which is connected to the linear motion feedthrough 14 by a cable 26. The exemplary drive controller 24 is manufactured by Huntington Mechanical Laboratories and includes a model MLC-1 indexer and a model SSP-500 hand held programmer. The exemplary linear motion feedthrough 14 provides a 20 pound load force capacity and a minimum drive velocity of 0.127 μm/s (i.e., 7.62 μm/min). This load force capacity and relatively slow drive speed are suitable for both push-in and push-out testing of the composite material 6. The indentor 20 pushes the end 12 of the individual fiber 22 at a predetermined velocity which is controlled by the drive controller 24.

The SEM 4 includes a vacuum chamber 28 for housing the fiber-matrix composite material 6 of FIG. 2 in a suitable vacuum. The vacuum chamber 28 is mounted on a vibration isolation table 29 which dampens out external vibrations for more accuracy in load recording. The vacuum chamber 28 also houses the feedthrough shaft 19 and the indentor 20 of the linear motion feedthrough 14, the load cell 16, an acoustic emission sensor 30, and a hot stage module 32. The vacuum chamber 28 provides an inert environment for elevated temperature testing of the composite material 6. The alignment guide 18 aligns the feedthrough shaft 19 through a passageway 33 in the rear of the vacuum chamber 28.

As will be explained in greater detail below with FIG. 6, the acoustic emission sensor 30 senses a precise time when the individual fiber 22 is debonded from the matrix 10 by the indentor 20 in a push-in or push-out operation. The acoustic emission sensor 30 is mounted adjacent the load cell 16 on the linear axis of the feedthrough shaft 19. The exemplary acoustic emission sensor 30 is manufactured by Physical Acoustics Corporation as model μ30. The load cell 16 senses a force applied by the indentor 20 to the end 12 of the individual fiber 22. A data acquisition computer 34 acquires this force with respect to time as the individual fiber 22 is pushed with respect to the matrix 10. This information provides a debonding load and a frictional sliding load between the individual fiber 22 and the matrix 10.

The indentor 20 is used to debond and slide the fibers 8 out of their surrounding matrix 10. Together, the indentor 20 and the load cell 16 provide and measure, respectively, the force between the fiber 22 and the matrix 10 during push-in and push-out operations. The indentor 20 is placed on the end 12 of the fiber 22, a load is applied by the indentor 20, and a debond failure between the fiber 22 and the matrix 10 occurs around the periphery of the fiber 22. Signals from the load cell 16 and the acoustic emission sensor 30 are collected by the data acquisition computer 34 through two cables 36,38, respectively. The exemplary data acquisition computer 34, which is an 80386SX personal computer (PC) or equivalent, includes an analog-to-digital (A/D) data acquisition board 39. The exemplary A/D data acquisition board 39, which is manufactured by Omega Engineering, Inc. as model WB-AAI-B, converts the analog signals from the load cell 16 and the acoustic emission sensor 30 to digital signals for use by the data acquisition computer 34.

The hot stage module 32 includes a digital temperature controller 40 which is connected to the hot stage module 32 by a cable 42. The hot stage module 32, which holds the fiber-matrix composite material 6, sits on a substage module 43 within the vacuum chamber 28. The substage module 43 provides tilt, rotate and two-axis positioning of the hot stage module 32 and, hence, the composite material 6.

The exemplary hot stage module 32 is manufactured by Oxford Instruments Limited as model H1005. The exemplary digital temperature controller 40, which is also manufactured by Oxford Instruments Limited as model ITC4, controls the temperature of the hot stage module 32 and, in turn, the temperature of the fiber-matrix composite material 6 to a preselected temperature between ambient room temperature and 1500° C. Preferably, the maximum temperature of the fibermatrix composite material 6 is approximately 1000° C. for proper operation of the SEM 4. Alternatively, the SEM 4 may be utilized for alignment of the indentor 20 with the end 12 of the fiber 22 at such temperature and, then, the temperature of the fiber-matrix composite material 6 may be increased to approximately 1500° C. for push-in or push-out testing. The hot stage module 32 also includes a specimen holder 44 as shown in FIG. 3.

The exemplary SEM 4, which is manufactured by Cambridge as StereoScan 90, Model B, also includes a plurality of controls 46, a backscatter electron detector 48, a secondary electron detector 50, and an X-ray detector system 52. The controls 46 control the position of the substage module 43 and the hot stage module 32 within the vacuum chamber 28. A digital imaging computer 54 is interconnected with the secondary detector 50 and the X-ray system 52 by two cables 56,57, respectively.

The exemplary digital imaging computer 54, which is an 80486DX PC or equivalent, facilitates capture and analysis of the digital image of the indentor 20, the fiber 22 and the matrix 10. The computer 54 is utilized, for example, to record the image of the individual fiber 22 and at least part of the matrix 10 before, during and after the time when the individual fiber 22 is debonded from and pushed out of the matrix 10.

Figure 3:
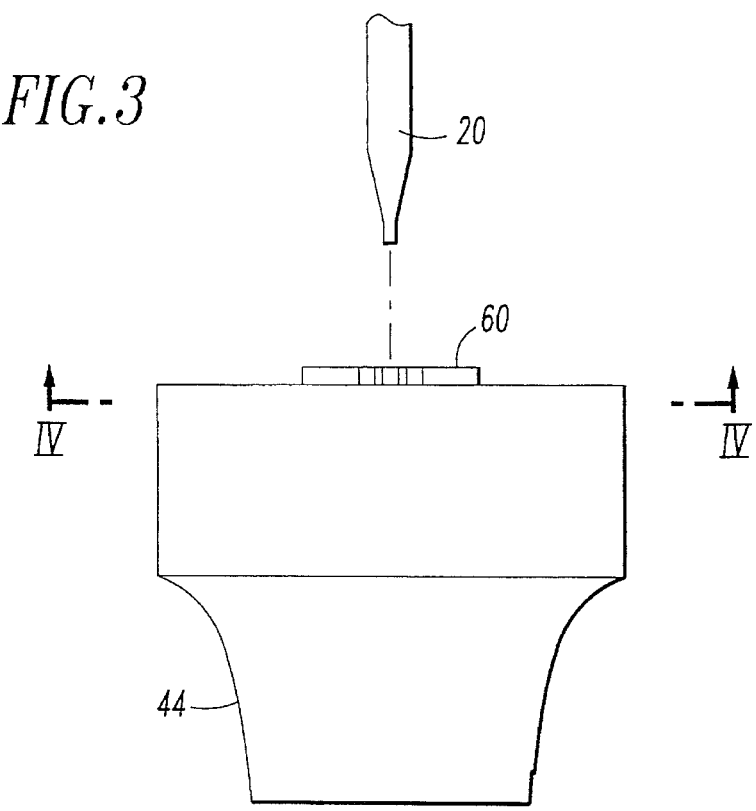
FIG. 3 is a side view of a scanning electron microscope specimen stub for a fiber-matrix composite material specimen in accordance with the invention.

FIG. 3 is a side view of the scanning electron microscope specimen stub 44 which holds a composite specimen 60 of the fiber-matrix composite material 6 of FIG. 2. The exemplary specimen 60 is prepared using computer controlled polishing equipment (not shown). Also referring to FIGS. 2 and 4, the fibers 8 are perpendicular to the polished surfaces 62, 64 of the exemplary specimen 60.

Also referring to FIG. 1, the high resolution digital imaging computer 54 facilitates the ease and preciseness of placement of the indentor 20 on the end 12 of the fiber 22 in the matrix 10. The digital imaging computer 54 includes an imaging system 58 and a PC card 59. The exemplary imaging system 58, which is manufactured by Elmdas as model DRV-2000, captures the digital image of the composite specimen 60. The exemplary PC card 59, which is marketed by Nucleus as a Personal Computer Analyzer Card, is interconnected with the X-ray system 52 and includes software for X-ray microanalysis of the composite specimen 60.

Figure 9:
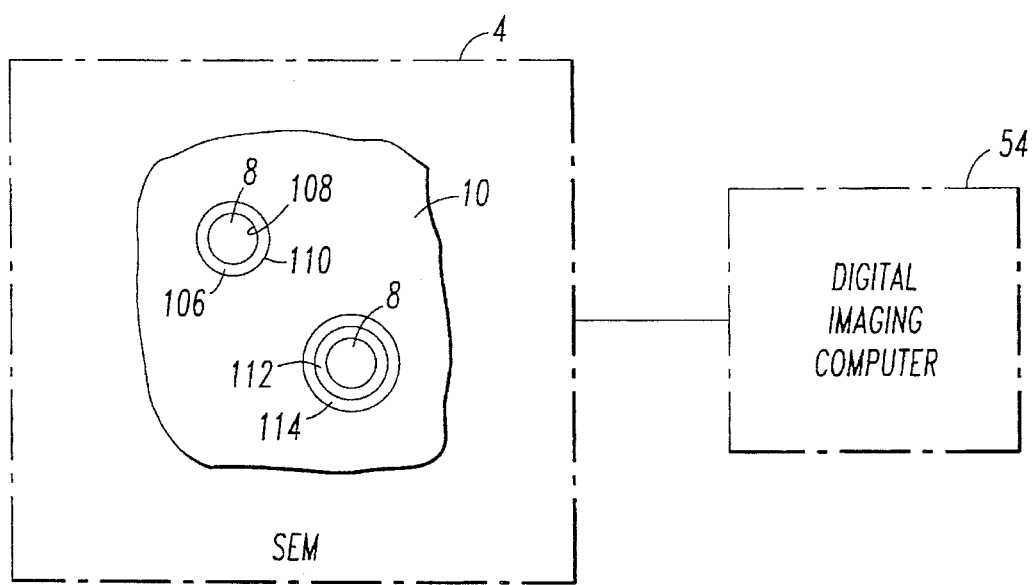
FIG. 9 is a top view of a fiber-matrix composite material.

The SEM 4 and the X-ray capabilities of the digital imaging computer 54 facilitate the identification of the interface where the fiber-matrix debonding occurs. For example, as shown in FIG. 9, where the fibers 8 have a single fiber coating 106, the SEM 4 and computer 54 define whether the debonding was at the coating surface 108 adjacent the fiber 8 or at the coating surface 110 adjacent the matrix 10. Otherwise, where the fibers 8 have multiple fiber coating layers 112, 114 of different chemistry, the SEM 4 and computer 54 detect the particular coating layer where the debonding occurred.

As shown in FIG. 4, the composite specimen 60 is adhesively attached to the exemplary specimen stub 44 for testing using a suitable adhesive 66. The specimen stub 44 includes a plurality of grooves 68 which accommodate the fibers which are pushed into (e.g., the fiber 8") the matrix 10 and which are pushed out of (e.g., the fiber 8') the matrix 10. The exemplary grooves 68, which are diamond sawed into the surface of the specimen stub 44, have a 200–400 μm width.

Figure 5:
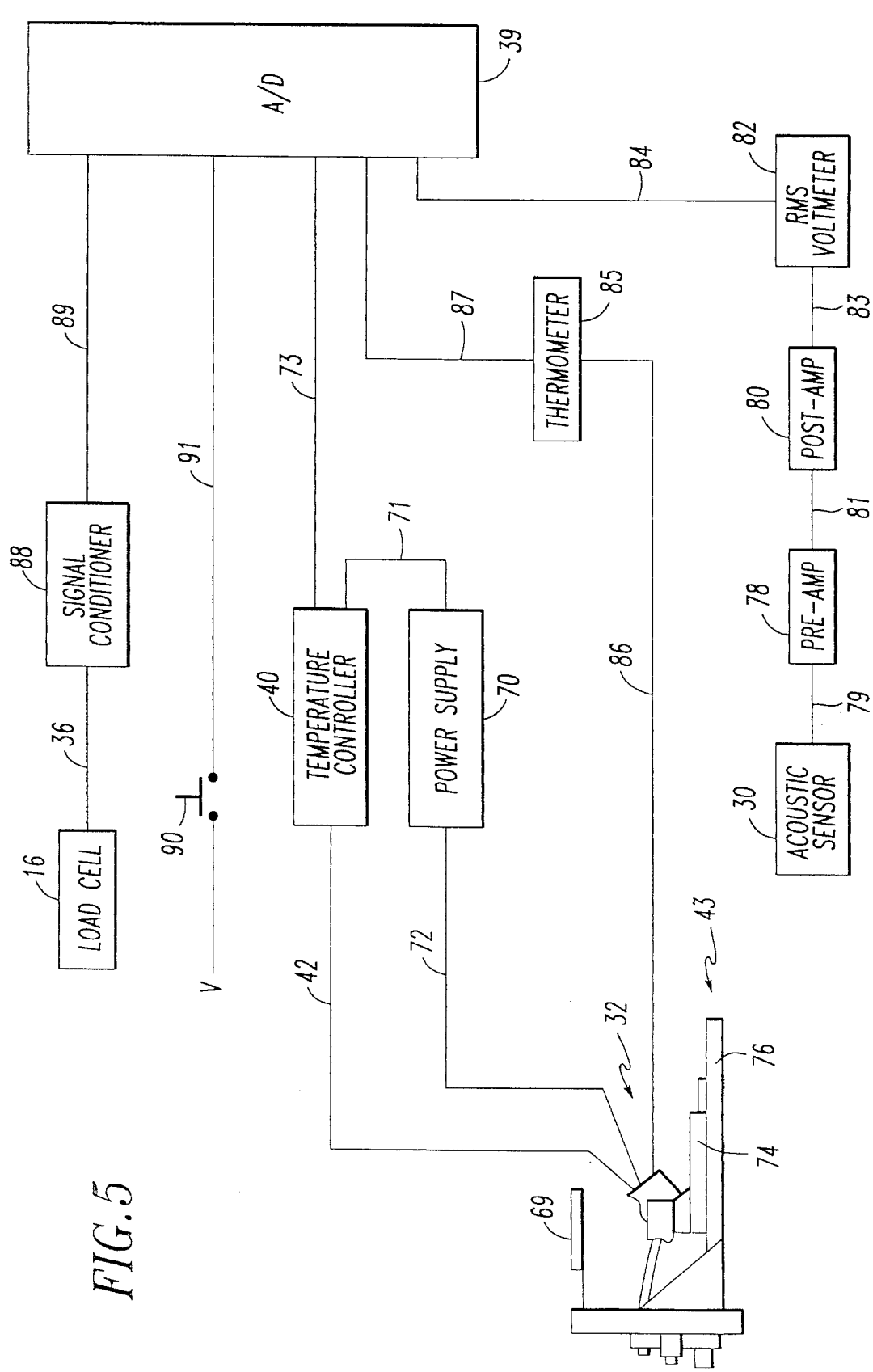
FIG. 5 is a schematic diagram of a hot stage module and related instrumentation for use in and with the scanning electron microscope of FIG. 1 in accordance with the invention.

FIG. 5 is a schematic diagram of the hot stage module 32 and related instrumentation for use in and with the SEM 4 of FIG. 1. The exemplary hot stage module 32 includes the digital temperature controller 40 of FIG. 1, a heat shield and shutter mechanism 69, and a power supply 70. The power supply 70 is connected to the digital temperature controller 40 and the hot stage module 32 by cables 71 and 72, respectively. The digital temperature controller 40 provides a signal, which is representative of the temperature of the composite specimen 60 of FIGS. 3–4, to the A/D data acquisition board 39 on a cable 73.

The substage module 43 includes an upper tilt/rotate substage 74 and a lower X–Y–Z positioning substage 76. The substage module 43 moves with 5 degrees of freedom in the various control axes for remote manipulation of the composite specimen 60 of FIGS. 3–4 within the vacuum chamber 28 of FIG. 1. The hot stage module 32 is mounted on the tilt/rotate substage 74.

The exemplary acoustic emission sensor 30 includes a low noise pre-amplifier 78, which is connected to the sensor 30 by a cable 79, and a post-amplifier 80. The post-amplifier 80 amplifies and filters a signal on a cable 81 from the pre-amplifier 78. The exemplary pre-amplifier 78 and post-amplifier 80 are manufactured by Physical Acoustics Corporation as models 1220A and AE1A, respectively. An RMS voltmeter 82 monitors a signal on a cable 83 from the post-amplifier 80 and provides a signal, representative of the output of the acoustic emission sensor 30, to the A/D data acquisition board 39 on a cable 84.

A digital thermometer 85 monitors a thermocouple signal, which is representative of the temperature of the hot stage module 32, on a cable 86. A conditioned signal, which is representative of the thermocouple temperature signal, is provided to the A/D data acquisition board 39 on a cable 87.

A signal conditioner 88 converts a signal from the load cell 16 on the cable 36 to a suitable signal on a cable 89 for the A/D data acquisition board 39. The exemplary signal conditioner 88 is manufactured by Sensotec as Model 450D.

Referring again to FIGS. 1–2, by observing the interface between the fiber 22 and the matrix 10 during loading by the indentor 20, an operator may note a load value at which cracking first begins at the fiber-matrix interface of the fiber 22 and, hence, the onset of movement of the fiber 22. The individual fiber 22 is pushed out of the matrix 10 using the indentor 20 at a constant displacement rate programmed in the drive controller 24 by the operator. The data acquisition computer 34 records both the load force versus time from the load cell 16 and the acoustic emission signal from the sensor 30. Accordingly, an exemplary method for sensing interfacial properties of the composite material 6 for the individual fiber 22, which has a diameter of $\leq 10$ μm, includes the steps of magnifying the composite material 6 in order to identify the end 12 of the fiber 22, aligning the indentor 20 with the end 12 and pushing the fiber 22 with respect to the matrix 10 with the indentor 20, and sensing the load force with the load cell 16 whenever the fiber 22 is pushed with respect to the matrix 10.

Figure 6:
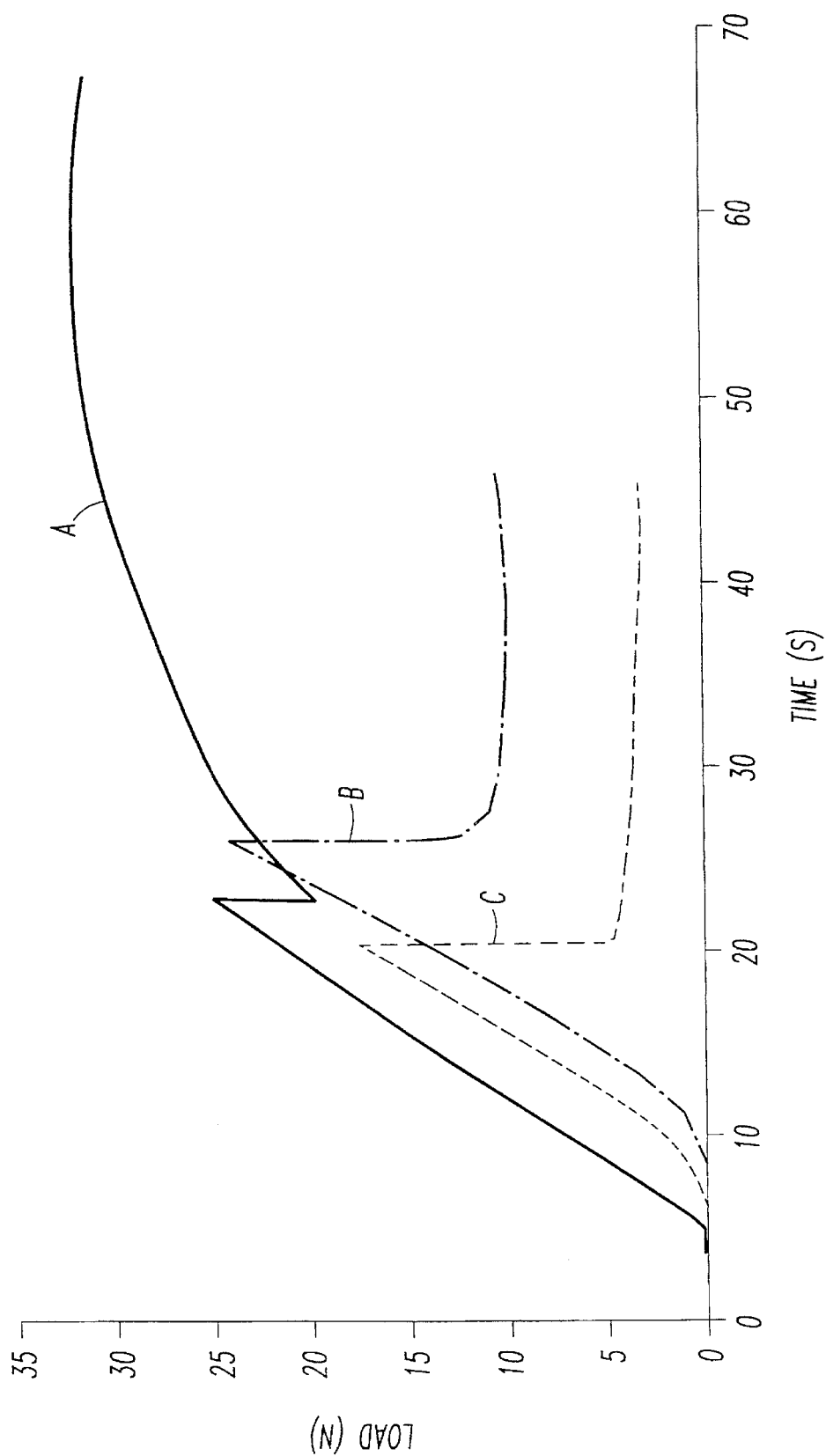
FIG. 6 is a graph of push-out load versus time for various temperatures of a fiber-matrix composite material in accordance with the invention.

FIG. 6 is a graph of push-out load versus time for various temperatures of the composite material 6 of FIG. 2. The vertical load axis is in newtons and the horizontal time axis is in seconds. Three exemplary load-time curves A, B and C for three respective exemplary temperatures 25° C., 480° C. and 650° C. are shown. Each of the curves A,B,C shows an instantaneous load drop which is associated with the debond of the fiber 22 from the matrix 10 of FIG. 2.

The acoustic emission sensor 30 of FIG. 1 senses the precise time when the fiber 22 is debonded from the matrix 10. The debonding load drop becomes more pronounced with increased temperature. The data after the debond event provides a record of the frictional loads as the fiber 22 slides out of the matrix 10. The higher temperature curves B,C show a steady state, or slowly decreasing, sliding stress. The ambient temperature curve A shows a rise in sliding stress after the initial debonding load drop. This suggests that the residual stresses (especially the radial clamping stresses) in the composite material 6 have a significant effect on sliding friction during push-out. The higher temperature curves B,C, hence, have less of a clamping effect, which decreases coating damage of the fiber 22.

The acoustic emission signal on the cable 84 of FIG. 5 detects the beginning of fiber-matrix interface cracking which is associated with the debonding event. This debonding event is recorded by the data acquisition computer 34 of FIG. 1 from the data acquisition board 39 and the signal on the cable 84. This event can also be visually noted by the operator using the high resolution of the SEM 4 of FIG. 1. The operator can then record the time this event occurred by using a switch 90 which selectively switches a voltage (V) on a cable 91 to the data acquisition board 39. The initial debonding load drop is a prelude to full fiber debonding and is used to calculate the interface "cracking stress".

Referring again to FIGS. 1–3, various interfacial property calculations are performed by the data acquisition computer 34 with a shear stress equation as shown below in Equation 1. Cracking stress, bond strength (i.e., interfacial shear strength) and sliding stress values are calculated using the load record of FIG. 6 and a "failure diameter" of the fiber 22. Equation 1 calculates these values and assumes a uniform shear strength along the length of the interface between the fiber 22 and the matrix 10. The load at the time when cracks were first observed in the fiber-matrix interface of the fiber 22 corresponds to the cracking stress. The bond strength is defined to be the peak load value before the load drops as the fiber 22 debonds and slides out of the matrix 10. The diameter of the debond (i.e., the fiber failure diameter) includes the original diameter of the fiber 22 plus any coating layers (not shown) that remain on it after debonding.

$$\sigma = L/(\pi D t) \quad \text{Eq. (1)}$$

where;

σ is the cracking stress, bond strength or sliding stress value;

L is the load at the point of interest;

D is the fiber failure diameter; and t is the thickness of the composite specimen 60.

The push-out method used with the exemplary apparatus 2 to perform the characterization of the fiber-matrix interface involves cutting a thin section (e.g., a thickness of 0.2 to 0.4 mm) of the composite material 6 at a right angle to the fibers 8. The sides of the composite specimen 60, both parallel and at right angles to the fibers 8, are ground and polished. The final thickness of the exemplary specimen 60 is between 0.04 and 0.40 mm. The specimen 60 is then mounted on the exemplary grooved specimen stub 44. Next, the specimen stub 44 is placed inside the vacuum chamber 28. An extended vacuum heat treatment (e.g., up to 1500° C.) or thermal cycling may be provided before testing of the composite specimen 60.

Figure 7:
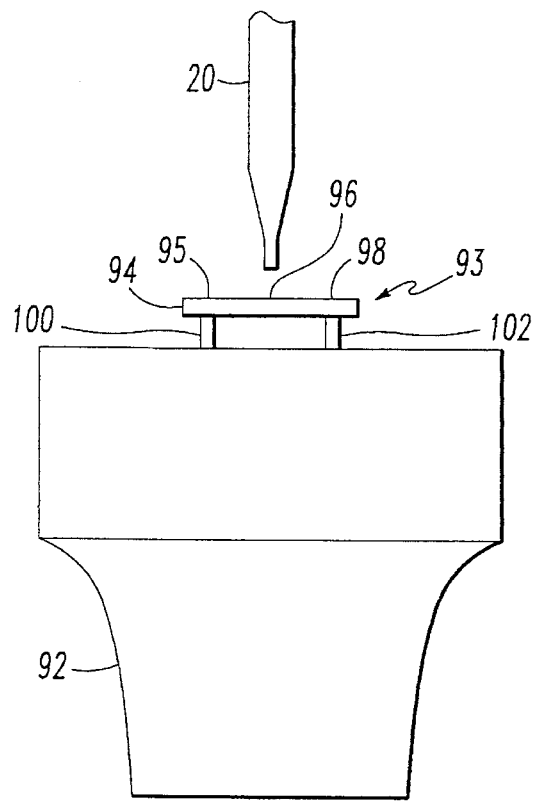
FIG. 7 is a side view of a scanning electron microscope specimen stub for a fiber in accordance with an alternative embodiment of the invention.

FIG. 7 is a side view of an alternative scanning electron microscope specimen stub 92 for a fiber 93 having a shaft 94. The alternative specimen stub 92 is used, in place of the specimen stub 44 of FIGS. 3–4, with the hot stage module 32. The hot stage module 32 is housed within the vacuum chamber 28 of the SEM 4 of FIG. 1. The specimen stub 92 facilitates measurements of properties of the fiber 93. The shaft 94 has a first support point 95, a push point 96 and a second support point 98. The push point 96 is between the first support point 95 and the second support point 98.

The specimen stub 92 includes a first support 100 for supporting the first support point 95 of the shaft 94 and a second support 102 for supporting the second support point 98 of the shaft 94. The indentor 20 pushes the push point 96 of the shaft 94 in order to bend the fiber 93. The load cell 16 of FIG. 1 senses a bending force which is applied to the shaft 94 by the indentor 20. The SEM 4 of FIG. 1 magnifies the shaft 94 in order to align the indentor 20 with the shaft 94.

Figure 8:
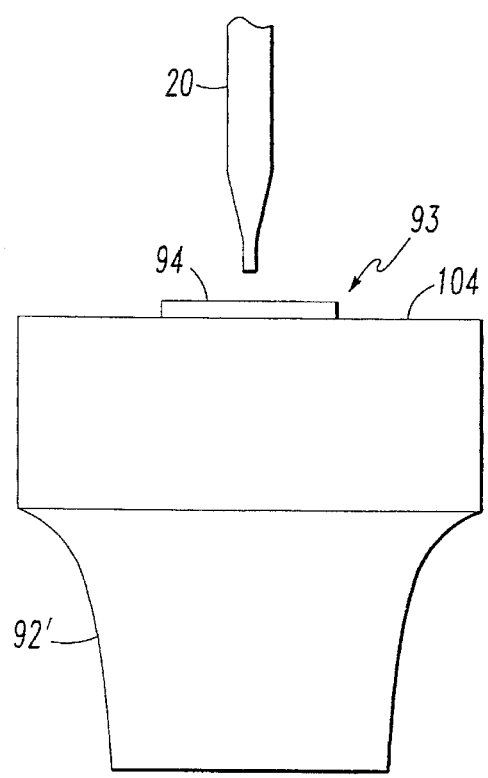
FIG. 8 is a side view of a scanning electron microscope specimen stub for a fiber in accordance with another alternative embodiment of the invention.

FIG. 8 is a side view of an alternative scanning electron microscope specimen stub 92' for the fiber 93. The alternative specimen stub 92' is used, in place of the specimen stub 44 of FIGS. 3–4, with the hot stage module 32. A surface 104 of the specimen stub 92' supports the shaft 94. The indentor 20 pushes the shaft 94 in order to crush the shaft 94 against the surface 104. The load cell 16 of FIG. 1 senses a crushing force which is applied to the shaft 94 by the indentor 20. The bending force of FIG. 7 and the crushing force of FIG. 8 are utilized in order to determine the mechanical properties (e.g., the tensile strength or the compressive strength) of the fiber 93.

Referring again to FIGS. 1–3, the exemplary apparatus 2 permits the testing of both relatively small diameter (e.g., ≦10 μm) and relatively large diameter (e.g., ≦140 μm) fibers 22 with superior alignment, imaging, load measurement and displacement control of the indentor 20. The apparatus 2 determines the interfacial bond strength and the sliding friction between the fiber 22 and the matrix 10. The resolution and depth of field of the exemplary SEM 4 make the alignment of the indentor 20 with the end 12 of the fiber 22 possible for the relatively small fiber diameters. The apparatus 2 further provides the capability of recording push-in and push-out tests at high magnification, digitally capturing images and X-ray analysis. The fibers 22 of the exemplary composite specimens 60 may be tested at a relatively slow exemplary displacement rate of 0.127 μm/s at a temperature up to 1500° C. These capabilities also allow detailed observation of the fiber–matrix interface while under load in order to both characterize and directly observe the failure process occurring at such interface.

While we have illustrated and described a present preferred embodiment of our invention, it is to be understood that we do not limit ourselves thereto and that our invention may be otherwise variously practiced within the scope of the following claims.

We claim:

1. Apparatus for use in measuring properties of a fiber-matrix composite material including a plurality of fibers in a matrix with at least one interface between each of the fibers and said matrix, each of the plurality of fibers has an end, said apparatus comprising:

pushing means for pushing the end of an individual fiber of the plurality of fibers with respect to the matrix;

sensing means for sensing at least one interfacial property of the fiber-matrix composite material whenever the individual fiber is pushed with respect to the matrix;

means for identifying the interface associated with debonding of the individual fiber from the matrix; and electron microscope means for magnifying the fiber-matrix composite material in order to align said pushing means with the end of the individual fiber and observe the interface during said pushing of the end of the individual fiber.

2. The apparatus of claim 1 wherein the individual fiber has a diameter less than about 10 μm; and wherein said pushing means includes an indentor having a diameter of about 7 μm for pushing the end of the individual fiber.

3. The apparatus of claim 1 wherein said pushing means is a linear motion feedthrough, the linear motion feedthrough having indentor means and drive controller means, the indentor means for pushing the end of the individual fiber at a predetermined velocity, the drive controller means for controlling the predetermined velocity.

4. The apparatus of claim 3 wherein said electron microscope means includes vacuum chamber means for housing the fiber-matrix composite material; and wherein the indentor means of the linear motion feedthrough is housed within the vacuum chamber means.

5. The apparatus of claim 4 wherein said pushing means is also for pushing the individual fiber of the plurality of fibers out of the matrix; wherein said sensing means includes load cell means housed within the vacuum chamber means for sensing a force applied by the indentor means to the end of the individual fiber; and wherein said sensing means includes data acquisition means for recording the force with respect to time as the individual fiber is pushed out of the matrix.

6. The apparatus of claim 4 wherein said sensing means includes acoustic sensor means housed within the vacuum chamber means for recording a time when the individual fiber is debonded from the matrix, and also includes imaging means for recording an image of the individual fiber and at least part of the matrix at about the time when the individual fiber is debonded from the matrix.

7. The apparatus of claim 4 wherein said electron microscope means includes hot stage module means housed within the vacuum chamber means for increasing the temperature of the fiber-matrix composite material.

8. The apparatus of claim 7 wherein the hot stage module means increases the temperature of the fiber-matrix composite material to about 1500° C.

9. The apparatus of claim 1 wherein said electron microscope means includes vacuum chamber means for housing the fiber-matrix composite material; and wherein said sensing means includes load cell means housed within the vacuum chamber means for sensing at least one of a debonding load between the individual fiber and the matrix and a frictional sliding load between the individual fiber and the matrix.

10. The apparatus of claim 1 wherein said pushing means provides up to about a 20 pound load force on the end of the individual fiber.

11. The apparatus of claim 1 wherein the individual fiber has a fiber coating with a first surface adjacent the individual fiber and a second surface adjacent the matrix; and wherein said means for identifying the interface identifies the surface at which the debonding occurred.

12. The apparatus of claim 1 wherein the individual fiber has a plurality of fiber coating layers; and wherein said means for identifying the interface identifies the coating layer at which the debonding occurred.

13. Apparatus for use in measuring properties of a fiber-matrix composite material including a plurality of fibers in a matrix with at least one interface between each of the fibers and said matrix, each of the plurality of fibers has an end, said apparatus comprising:

pushing means for pushing the end of at least one fiber of the plurality of fibers with respect to the matrix;

sensing means for sensing an interfacial property of the fiber-matrix composite material whenever the at least one fiber is pushed with respect to the matrix;

X-ray means for identifying the interface associated with debonding of the at least one fiber from the matrix: and magnification means for magnifying the fiber-matrix composite material in order to align said pushing means with the end of the at least one fiber and observe the interface during said pushing of the end of the at least one fiber.

14. Apparatus for use in measuring properties of a fiber for a fiber-matrix composite material, the fiber including a shaft having a longitudinal portion, said apparatus comprising:

pushing means for pushing the longitudinal portion of the shaft of the fiber;

sensing means for sensing a force applied by said pushing means to the longitudinal portion of the shaft of the fiber; and magnification means for magnifying the longitudinal portion of the shaft of the fiber in order to align said pushing means with the longitudinal portion of the shaft of the fiber.

15. The apparatus of claim 14 wherein the shaft of the fiber has a first support point, a push point and a second support point, the push point being between the first support point and the second support point; wherein said magnification means includes first support means for supporting the first support point of the shaft and second support means for supporting the second support point of the shaft; wherein said pushing means pushes the push point of the shaft in order to bend the fiber; and wherein said sensing means senses a bending force which is applied to the shaft by said pushing means.

16. The apparatus of claim 14 wherein said magnification means includes support means for supporting at least part of the shaft of the fiber; wherein said pushing means pushes the shaft of the fiber in order to crush the shaft against the support means; and wherein said sensing means senses a crushing force which is applied to the shaft by said pushing means.

17. Method for sensing at least one interfacial property of a fiber-matrix composite material including a plurality of fibers in a matrix with at least one interface between each of the fibers and said matrix, the plurality of fibers having an end, said method comprising the steps of:

magnifying the fiber-matrix composite material in order to identify the end of an individual fiber of the plurality of fibers;

aligning an indentor with the end of the individual fiber;

pushing the end of the individual fiber with respect to the matrix with the indentor;

employing X-ray means to identify the interface associated with debonding of the individual fiber from the matrix;

sensing at least one interfacial property of the fiber-matrix composite material whenever the individual fiber is pushed with respect to the matrix; and observing the interface during said pushing of the end of the individual fiber.

18. The method of claim 17 further comprising the steps:

employing the individual fiber with a fiber coating having a first surface adjacent the individual fiber and a second surface adjacent the matrix; and identifying the surface at which the debonding occurred.

19. The method of claim 17 further comprising the steps:

employing the individual fiber with a plurality of fiber coating layers; and identifying the coating layer at which the debonding occurred.

20. Apparatus for use in measuring properties of a support material including at least one member which is supported by the support material, the at least one member having a surface, with at least one interface between each of the members and the support material, said apparatus comprising:

pushing means for pushing the surface of the at least one member with respect to the support material;

sensing means for sensing at least one property of the at least one member whenever the at least one member is pushed with respect to the support material;

means for identifying the interface associated with debonding of the at least one member from the support material: and electron microscope means for magnifying the support material in order to align said pushing means with the surface of the at least one member and observe the interface during said pushing of the surface of the at least one member.

* * * * *